(12) United States Patent
Hsueh et al.

(10) Patent No.: US 8,225,675 B2
(45) Date of Patent: Jul. 24, 2012

(54) CONTROLLED SHEAR/TENSION FIXTURE

(75) Inventors: Chun-Hway Hsueh, Knoxville, TN (US); Chain-tsuan Liu, Knoxville, TN (US); Easo P. George, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 352 days.

(21) Appl. No.: 12/555,070

(22) Filed: Sep. 8, 2009

(65) Prior Publication Data

US 2011/0056304 A1    Mar. 10, 2011

(51) Int. Cl.
  *G01N 3/24* (2006.01)
(52) U.S. Cl. .......................................... 73/841
(58) Field of Classification Search .............. 73/841
  See application file for complete search history.

(56) References Cited

U.S. PATENT DOCUMENTS

| | | | | |
|---|---|---|---|---|
| 3,910,124 | A * | 10/1975 | Halsey | 73/601 |
| 4,637,252 | A * | 1/1987 | Rhee et al. | 73/150 A |
| 5,602,341 | A * | 2/1997 | Lee et al. | 73/850 |
| 5,739,436 | A * | 4/1998 | Trautwein | 73/841 |
| 6,021,661 | A * | 2/2000 | Lowell et al. | 73/38 |
| 6,681,618 | B2 * | 1/2004 | Hajduk et al. | 73/54.37 |
| 7,650,795 | B2 * | 1/2010 | Abousleiman et al. | 73/841 |

OTHER PUBLICATIONS

C.H. Hsueh, et al., Shear Fracture of Bulk Metallic Glasses with Controlled Applied Normal Stresses, www.ScienceDirect.com, Scripta Materialia 59 (2008) 111-114 (4 pages).
C.H. Hsueh, et al., Controlled Normal/Shear Loading and Shear Fracture in Bulk Metallic Glasses, ScienceDirect, Intermetallics 17 (2009) 802-810 (9 pages).

* cited by examiner

*Primary Examiner* — Lisa Caputo
*Assistant Examiner* — Octavia Davis-Hollington
(74) *Attorney, Agent, or Firm* — Luedeka Neely Group, P.C.

(57) ABSTRACT

A test fixture for simultaneously testing two material test samples is provided. The fixture provides substantially equal shear and tensile stresses in each test specimens. By gradually applying a load force to the fixture only one of the two specimens fractures. Upon fracture of the one specimen, the fixture and the load train lose contact and the second specimen is preserved in a state of upset just prior to fracture. Particular advantages of the fixture are (1) to control the tensile to shear load on the specimen for understanding the effect of these stresses on the deformation behavior of advanced materials, (2) to control the location of fracture for accessing localized material properties including the variation of the mechanical properties and residual stresses across the thickness of advanced materials, (3) to yield a fractured specimen for strength measurement and an unfractured specimen for examining the microstructure just prior to fracture.

10 Claims, 5 Drawing Sheets

CONTROLLED SHEAR/TENSION FIXTURE

GOVERNMENT RIGHTS

This invention was made with government support under Contract No. DE-AC05-00OR22725 awarded by the U.S. Department of Energy. The government has certain rights in the invention.

FIELD

This disclosure relates to the field of material strength testing. More particularly, this disclosure relates to tests for shear and tensile strength.

BACKGROUND

The assessment of advanced materials often benefits from an analysis of stresses that result from different operational conditions. Often these stresses are induced by a combination of shear forces and tensile forces. Often these stresses are different in different portions of articles made from such materials. Current test fixtures typically are not able to assess various combinations of these characteristics. What are needed therefore are improved test fixtures for assessing the mechanical strength of materials.

SUMMARY

The present disclosure provides a fixture for imposing tensile and shear stresses on a material. The fixture includes a first block disposed adjacent a base surface. The first block has a first test specimen mounting portion with a first attaching mount for receiving a first test specimen. The first block also has a second test specimen mounting portion that is disposed distal from the first test specimen mounting portion. The second test specimen mounting portion has a second attaching mount for receiving a second test specimen. The first test specimen mounting portion and the second test specimen mounting portion are substantially immovably fixed with respect to each other. There is a second block disposed between the first test specimen mounting portion and the second test specimen mounting portion. The second block has a third test specimen mounting portion having a third attaching mount for receiving the first test specimen and a fourth attaching mount for receiving the second test specimen. When the first test specimen is disposed in the first attaching mount and the third attaching mount and the second test specimen is disposed in the second attaching mount and the fourth attaching mount the second block is disposed offset from the base surface, and the second block moves with respect to the first block when a force is applied to the second block.

Also provided is a method of imposing near fracture tensile and shear stresses in a material test specimen. The method includes a step of loading two substantially identical test specimens in a test fixture that is configured to impose substantially identical shear and tensile stresses in each test specimen. The method also includes a step of loading the two test specimens with substantially identical shear and tensile stresses until only one of the test specimens fractures thereby allowing for the examination of the unfractured specimen just prior to fracture.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein.

DETAILED DESCRIPTION

In the following detailed description of the preferred embodiments, reference is made to the accompanying drawings, which form a part hereof, and within which are shown by way of illustration the practice of specific embodiments of fixtures for imposing tensile and shear stresses on a material. It is to be understood that other embodiments may be utilized, and that structural changes may be made and processes may vary in other embodiments.

Figure 1:
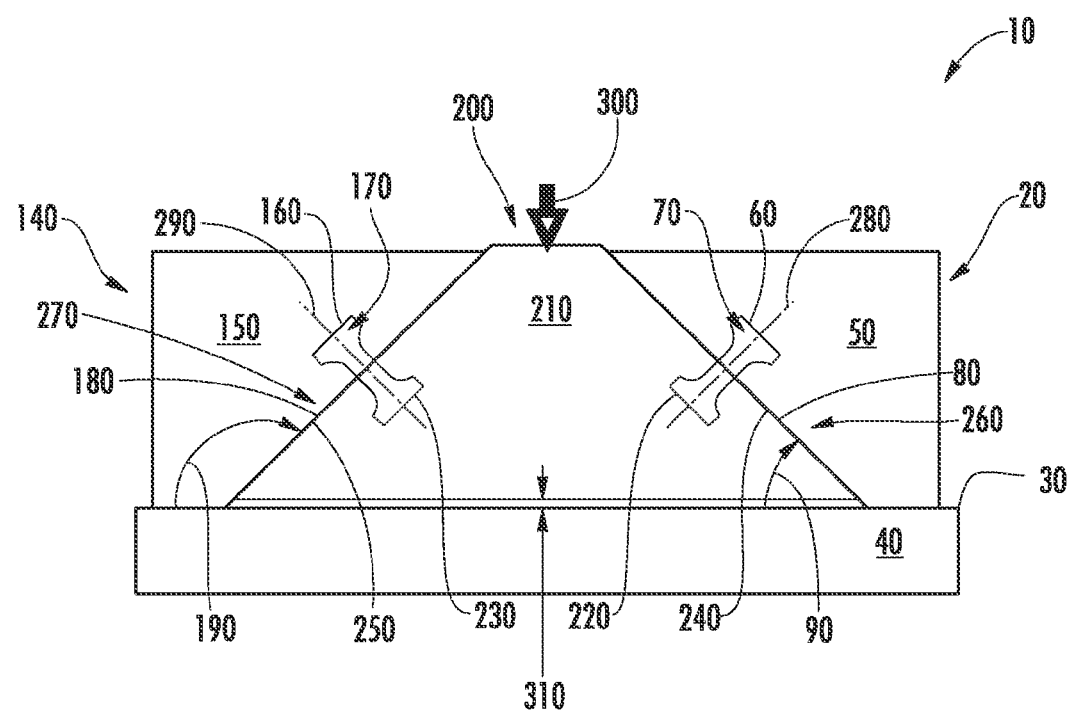
FIG. 1 is a somewhat schematic front view of a controlled shear/tension test fixture.

For many advanced materials the ability to control the location of shear fracture enables a systematic study of the effects of varying compositions, microstructures, and residual stresses on the yield and fracture strengths of such materials. Also, it is often very useful to examine the state of the materials just prior to fracture. This is especially true for non-ductile materials such as glass or ceramics. FIG. 1 illustrates a front view of a test fixture that is useful for these purposes. The fixture 10 includes a first block 20 that is disposed adjacent a base surface 30. In the embodiment of FIG. 1, the base surface 30 is a surface on a test platform 40. In other embodiments the base surface 30 may be a surface on the first block 20.

The first block 20 includes a first test specimen mounting portion 50 with a first attaching mount 60 for receiving a first test specimen 70. The first block 20 also includes and a first reference surface 80 that is disposed at a first angle 90 to the base surface 30. Typically the first angle (e.g., the first angle 90) is an acute angle. The first block 20 also includes a second test specimen mounting portion 150 that is disposed distal from the first test specimen mounting portion 50. The second test specimen mounting portion 150 has a second attaching mount 160 for receiving a second test specimen 170 and a second reference surface 180 that is disposed at a second angle 190 to the base surface 30. In the embodiment of FIG. 1 the second angle 190 is supplementary to the first angle 90. (That is, the sum of the first angle 90 in degrees plus the second angle 190 in degrees equals 180 degrees.) In the embodiment of FIG. 1 the first angle 90 is an acute angle and the second angle 190 is an obtuse angle. In some embodiments the first angle 90 and the second angle 190 may each be substantially 90° angles. In the embodiment of FIG. 1 the first reference surface 80 and the second reference surface 180 are substantially straight, flat surfaces; in other embodiments the first reference surface 80 and the second reference surface 180 may not be straight, flat surfaces. In most embodiments the first test specimen mounting portion 50 and the second test specimen mounting portion 150 are substantially immovably fixed with respect to each other.

The test fixture 10 also has a second block 200 that is disposed between the first test specimen mounting portion 50 and the second test specimen mounting portion 150. The second block 200 has a third test specimen mounting portion 210. The third test specimen mounting portion 210 has a third attaching mount 220 for receiving the first test specimen 70 and a fourth attaching mount 230 for receiving the second test specimen 170. The third test specimen mounting portion 210 also has a third reference surface 240 that is disposed adjacent the first reference surface 80 at substantially the first angle 90 from the base surface 30 and a fourth reference surface 250 that is disposed adjacent the second reference surface 180 at substantially the second angle 190 from the base surface 30. The combination of the two reference surfaces 80 and 240 is referred to herein as a first tilt interface 260, and the combination of the two reference surfaces 180 and 250 is referred to herein as a second tilt interface 270. In the embodiment of FIG. 1 the third reference surface 240 and the fourth reference surface 250 are substantially straight, flat surfaces; in other embodiments the third reference surface and the fourth reference surface may not be straight, flat surfaces. In some embodiments the first test specimen 70 has a first longitudinal axis 280 and the first longitudinal axis 280 is disposed normal to the first tilt interface 260. In preferred embodiments the second test specimen 170 has a second longitudinal axis 290 and the second longitudinal axis 290 is disposed normal to the second tilt interface 270.

In the embodiment of FIG. 1, the first test specimen mounting portion 50 and the second test specimen mounting portion 150 are formed as two congruent right-angle trapezoidal structures at opposing ends of the fixture 10. The third test specimen mounting portion 210 is formed as a single isosceles trapezoidal structure. The first attaching mount 60, the second attaching mount 160, the third attaching mount 220, and the fourth attaching mount 230 allow for two test specimens (test specimens 70 and 170) to be loaded simultaneously.

When the test specimens 70 and 170 are mounted in the fixture 10, the second block 200 protrudes slightly above the first block 20 as shown in FIG. 1. This facilitates the process of applying a downward loading force 300 on the second block 200 only. The second block is disposed slightly above (by offset 310) the base surface 30. When the downward loading force 300 is applied normal to the base surface 30, and the first angle 90 and the second angle 190 are supplementary angles, the first test specimen 70 and the second test specimen 170 each receive equal tensile and shear forces until one or both specimens fracture. If the first test specimen 70 and the second test specimen 170 are substantially identical in composition and geometry, fracturing may be limited to only one of the two specimens by gradually increasing the downward loading force 300. Upon fracture of the one specimen, the second block 200 and the load train lose physical contact so no further force is applied to the un-fractured specimen. This has the effect of removing the load force prior to fracture of the test specimen that is not fractured. Thus the un-fractured specimen is preserved in a state of upset that exists just prior to fracture.

A further beneficial characteristic of the fixture 10 is that during the process of applying the downward loading force 300, gaps are established between the third test specimen mounting portion 210 and the first test specimen mounting portion 50 and between the third test specimen mounting portion 210 and the second test specimen mounting portion 150. Consequently there is no contact (or friction) between these components. This is important because it ensures that the downward loading force 300 is applied totally on the two test specimens. Hence, while the fractured specimen gives the strength data, the un-fractured specimen can be used to study the microstructure just prior to fracture.

Figure 2:
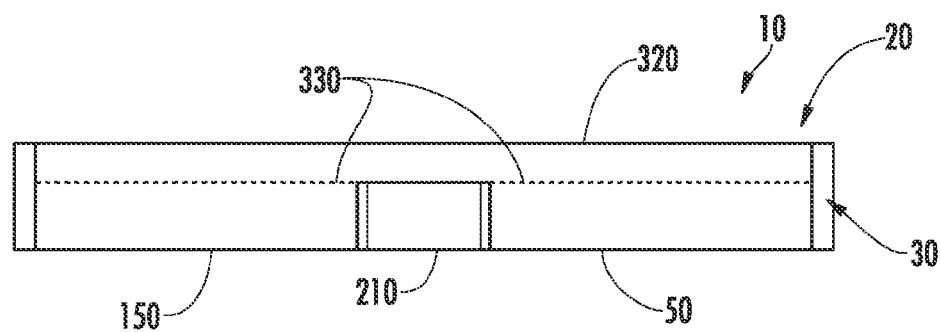
FIG. 2 is a somewhat schematic top view of the test fixture of FIG. 1

FIG. 2 illustrates a top view of the fixture 10. In the embodiment of FIGS. 1 and 2, the first block 20 is fabricated with a backing plate 320. The first test specimen mounting portion 50 and the second test specimen mounting portion 150 are fabricated from two elements that are attached to the backing plate 320 at joint lines 330. In other embodiments the first block 20 may be machined or cast or otherwise formed as a single piece of material. However, removably attaching a first test specimen mounting portion (e.g., the first test specimen mounting portion 50) and a second test specimen mounting portion (e.g., the second test specimen mounting portion 150) to a backing plate (e.g., the backing plate 320) is preferred because it facilitates removal of the test specimens 70 and 170 after testing. Such removable attachment may, for example, be accomplished with attachment means such as bolts, studs, or clamps.

Figure 3:
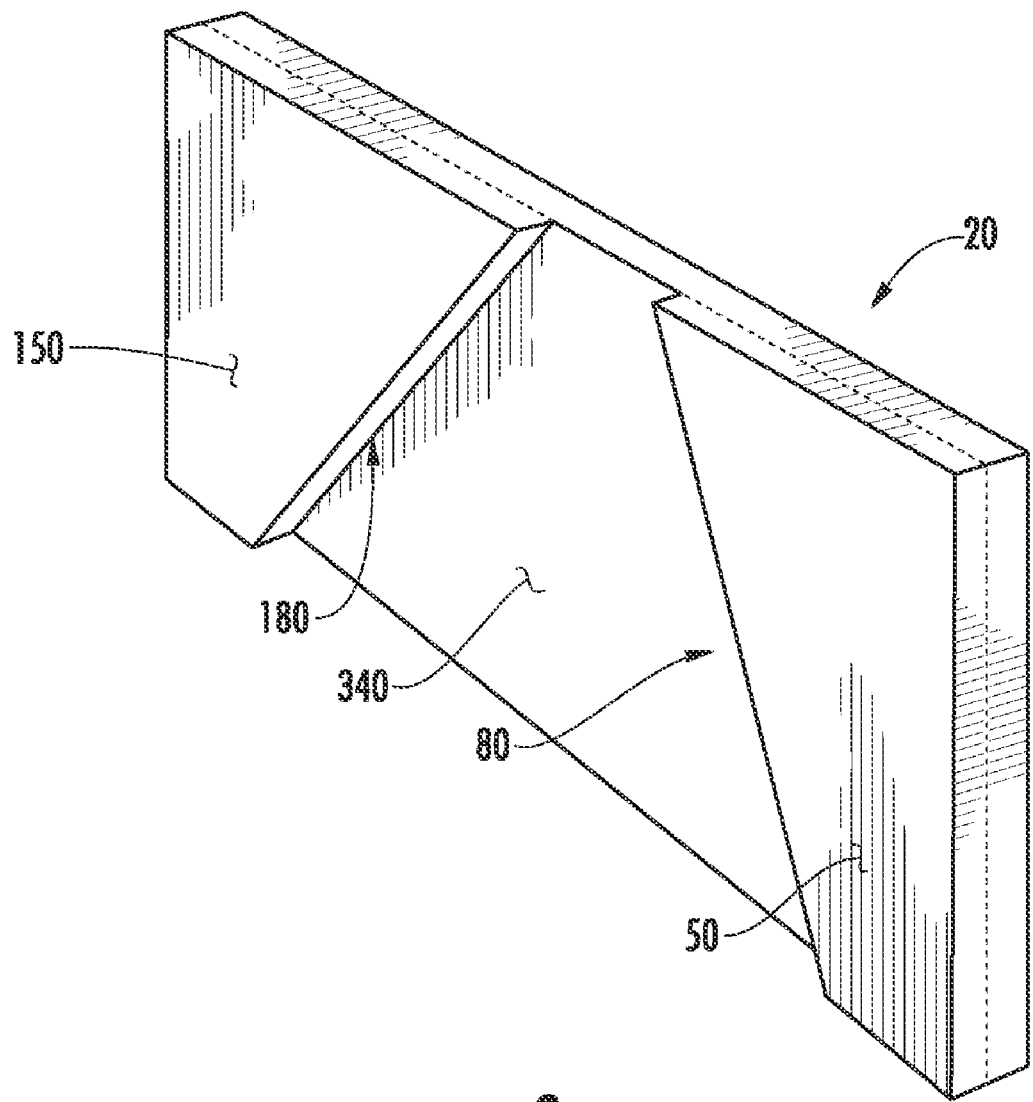
FIG. 3 is a somewhat schematic perspective view of a portion of the test fixture of FIG. 1 and FIG. 2.

FIG. 3 illustrates a perspective view of the first block 20. For simplicity of illustration the first attaching mount 60 and the second attaching mount 160 are not depicted. FIG. 3 illustrates a further view of the first reference surface 80 and the second reference surface 180. FIG. 3 also illustrates a recessed area 340 in the first block 20 and the first reference surface 80 and the second reference surface 180 are disposed in the recessed area 340.

Figure 4:
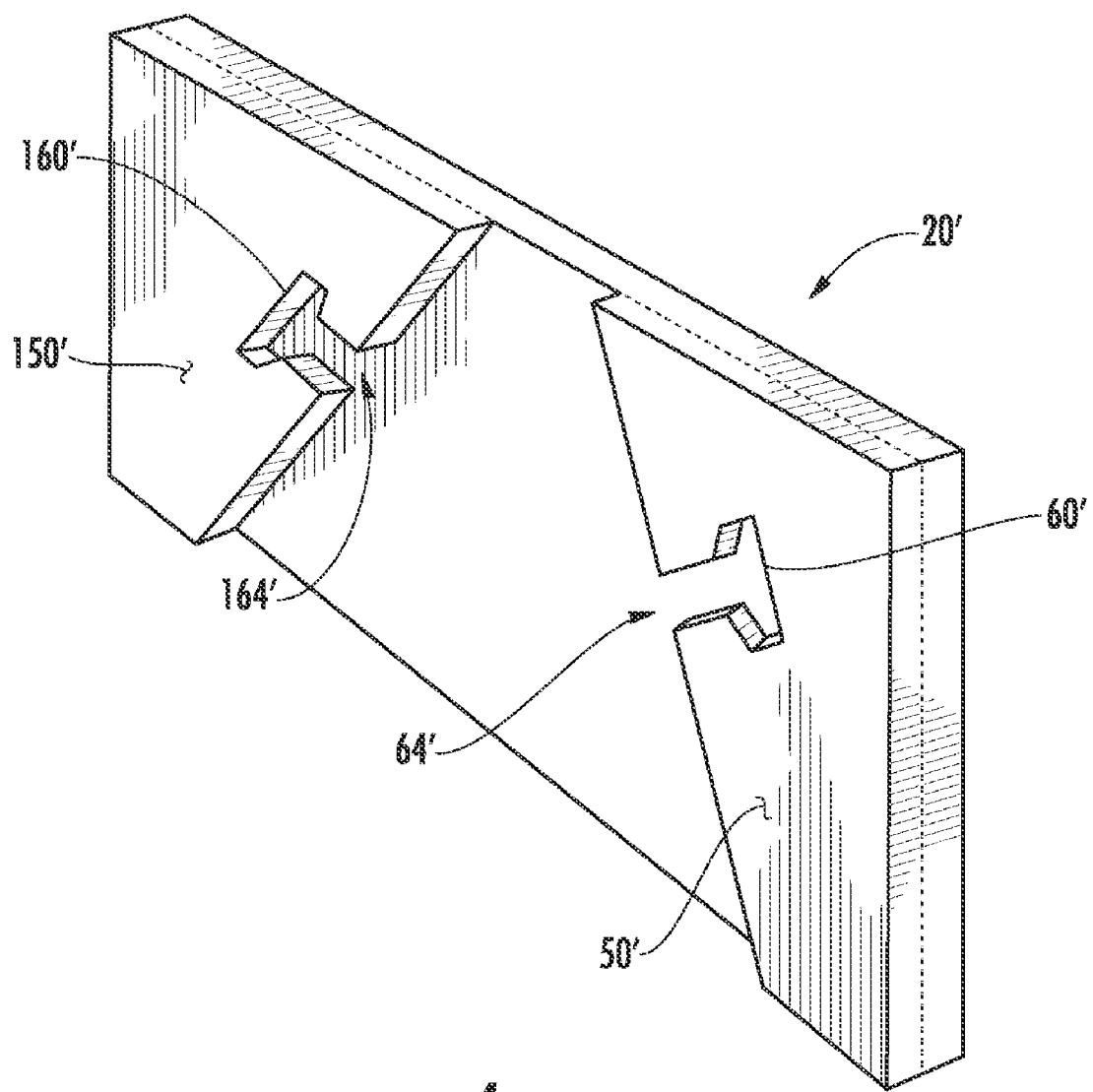
FIG. 4 is a somewhat schematic perspective view of a portion of a test fixture.

FIG. 4 illustrates a perspective view of a first block 20'. The first block 20' is similar to the first block 20 of FIGS. 1, 2, and 3, except that the first block 20' has a first attaching mount 60' that is a slightly different shape than the first attaching mount 60 of the first block 20, and the second attaching mount 160' of the first block 20' is a slightly different shape than the second attaching mount 160 of the first block 20. FIG. 4 illustrates how the first attaching mount 60' comprises a first test specimen mounting recess 64' in the first test specimen mounting portion 50' and the second attaching mount 160' comprises a second test specimen mounting recess 164' in the second test specimen mounting portion 150'.

Figure 5:
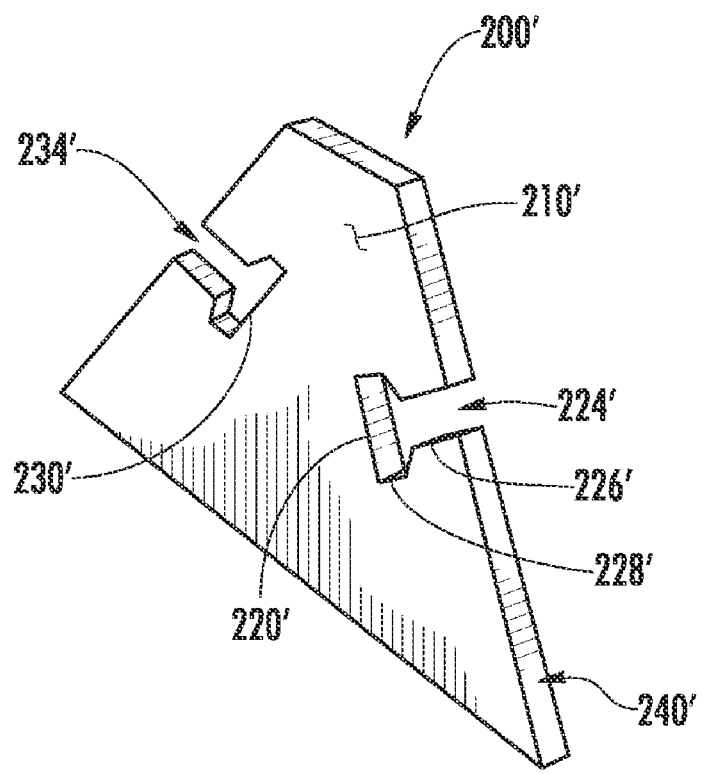
FIG. 5 is a somewhat schematic perspective view of a portion of a test fixture.

FIG. 5 illustrates a perspective view of a second block 200'. The second block 200' is similar to the second block 200 of FIGS. 1, 2, and 3 except that the second block 200' has a third attaching mount 220' that is a slightly different shape than the third attaching mount 220 of the second block 200, and the second block 200' has a fourth attaching mount 230' that is a slightly different shape than the fourth attaching mount 230 of the second block 200. The third attaching mount 220' has a third test specimen mounting recess 224' in the third test specimen mounting portion 210' and the fourth attaching mount 230' has a fourth test specimen mounting recess 234' in the third test specimen mounting portion 210'.

The first attaching mount 60, the first attaching mount 60', the second attaching mount 160, the second attaching mount 160', the third attaching mount 220, the third attaching mount 220', the fourth attaching mount 230, and the fourth attaching mount 230' are referred to as "half-dog-bone shaped mounting recesses." Half-dog-bone shaped mounting recesses are characterized as having a neck portion (e.g., neck portion 226' in FIG. 5) adjacent a reference surface (e.g., third reference surface 240' in FIG. 5) and a flared portion (e.g., flared portion 228' in FIG. 5). In other embodiments, other attaching mount shapes for other test specimen geometries may be used. The half-dog-bone-shaped recesses of the first attaching mount 60, the second attaching mount 160, the third attaching mount 220, and the fourth attaching mount 230 are generally preferred over the first attaching mount 60', the second attaching mount 160', the third attaching mount 220', and the fourth attaching mount 230' because the curved shape of the neck portions of the first attaching mount 60, the second attaching mount 160, the third attaching mount 220, and the fourth attaching mount 230 reduce stress concentration in the test specimens.

Referring again to FIG. 1, upon applying a downward loading force 300 on the top surface of the second block 200, a downward motion of the central block results in a shear displacement parallel to each of the two tilt interfaces 260 and 270. Fracture of one of the test specimens is expected to occur either between the first reference surface 80 and the third reference surface 240 or between the second reference surface 180 and the fourth reference surface 250. Because the location of the shear fracture is substantially controlled by the fixture (e.g. fixture 10 of FIG. 1) test specimens may be fabricated to cause fracturing at a specific area of interest in a test material, such as at a reinforced region, or at a weak region, or at another structural transition zone in a material, or at various locations subjected to different residual stresses. This is very useful for assessing localized material properties.

Figure 6:
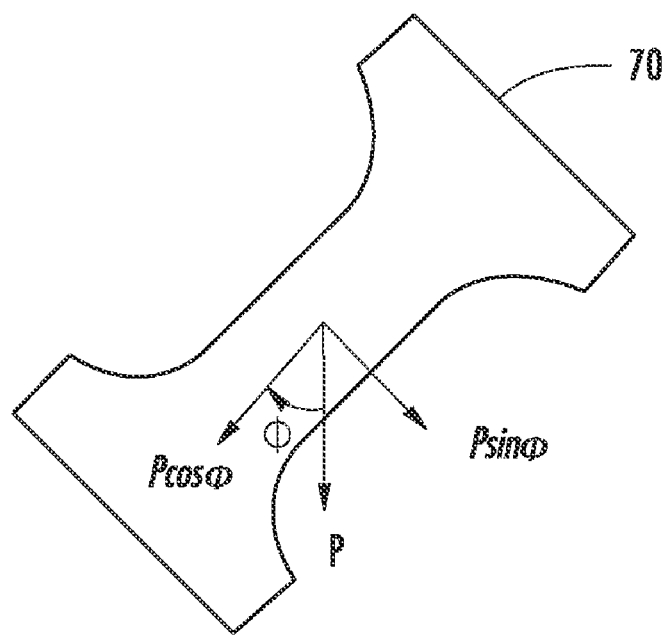
FIG. 6 is a force vector diagram illustrating tensile and shear stresses induced in a test specimen.

As illustrated in FIG. 6, the resolved forces on each test specimen are determined by the inclined angles 90 and 190, where $\phi$ is the angle 90. For an applied downward loading force 300 of 2 P, the resolved tensile and shear loads on the specimen are $P \cos \phi$ and $P \sin \phi$, respectively, as shown in FIG. 6. Different ratios of the tensile to shear load on the specimen may be achieved by varying the inclined angle, $\phi$ (i.e., angle 90) of the tilt interface. Thus, this fixture is particularly beneficial in that it can impose different stress ratios on the specimen to characterize the mechanical behavior of materials. Note that varying the included angle $\phi$ (i.e., angle 90) of the tilt interface results in a corresponding variation in the angle 190, because the first angle 90 and the second angle 190 are supplementary.

Figure 7:
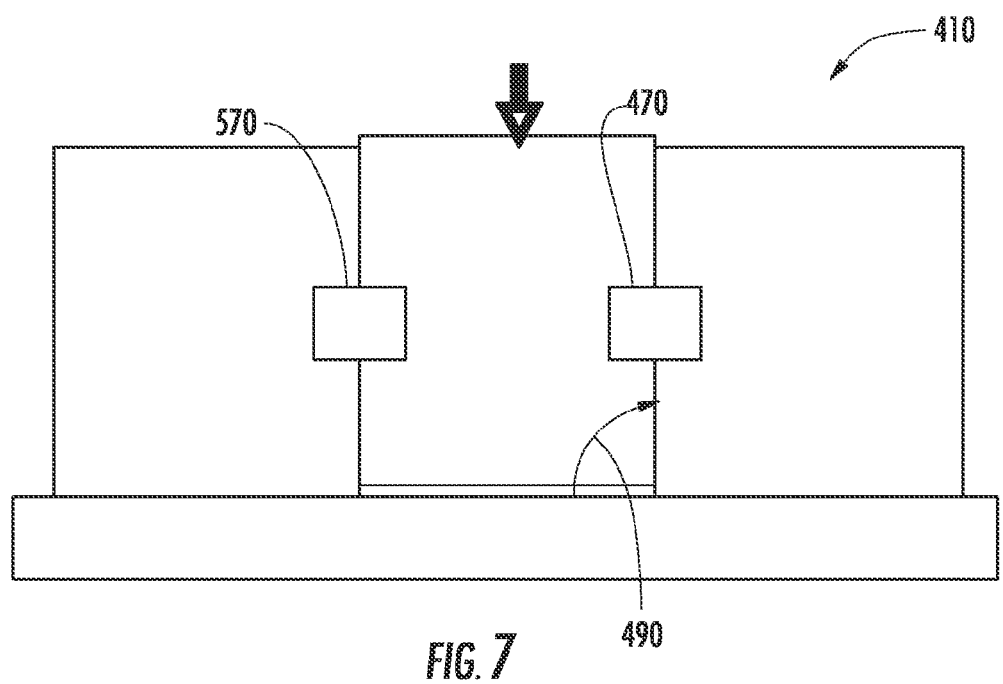
FIG. 7 is a somewhat schematic view of a controlled shear/tension test fixture.
Figure 8:
FIG. 8 is a somewhat schematic top view of the test fixture of FIG. 7.

A further embodiment of a controlled shear/tension fixture is the test fixture 410 depicted in FIG. 7 (front view) and FIG. 8 (top view). In this embodiment the inclined angle, $\phi$ (490) is 90°, and the test specimens 470 and 570 are subjected to shear force only. In the embodiment of FIG. 7, the test specimens 470 and 570 have a simple rectangular shape.

The fixture 10 of FIGS. 1 and 2 and the fixture 410 of FIG. 7 may be used to perform a method of imposing near fracture tensile and shear stresses in a material test specimen. This may be accomplished by loading two substantially identical test specimens in a test instrument such as fixture 10 or fixture 410 that is configured to impose substantially identical shear and tensile stresses in each specimen. Then the two test specimens may be loaded with substantially identical shear and tensile stresses. However, due to either intentional design considerations or variability due to manufacturing tolerances, the two specimens will have cross sectional areas that are not exactly identical. In general, the specimen with the smaller cross sectional area will fail first and the other specimen remains un-fractured. The test specimen that did not fracture may then be examined for the effects of near fracture tensile and shear stresses.

In summary, embodiments disclosed herein describe various test fixtures for assessing the mechanical strength of materials where both shear stresses and tensile stresses may be applied simultaneously to test specimens. The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A fixture for imposing shear stresses on a material, comprising:
    a first block disposed adjacent a base surface and having
        a first test specimen mounting portion with a first attaching mount for receiving a first test specimen and a first reference surface disposed at a first angle to the base surface and
        a second test specimen mounting portion disposed distal from the first test specimen mounting portion, the second test specimen mounting portion having a second attaching mount for receiving a second test specimen and a second reference surface disposed at a second angle to the base surface, where the second angle is supplementary to the first angle, wherein the first test specimen mounting portion and the second test specimen mounting portion are substantially immovably fixed with respect to each other; and
    a second block disposed offset from the base surface and between the first test specimen mounting portion and the second test specimen mounting portion, the second block having
        a third test specimen mounting portion having a third attaching mount for receiving the first test specimen, and a fourth attaching mount for receiving the second test specimen, and a third reference surface disposed adjacent the first reference surface at substantially the first angle to the base surface, and a fourth reference surface disposed adjacent the second reference surface at substantially the second angle to the base surface such that
    when (a) the first test specimen is disposed in the first attaching mount and the third attaching mount and (b) the second test specimen is disposed in the second attaching mount and the fourth attaching mount, the second block moves with respect to the first block when a downward loading force is applied to the second block.

2. The fixture of claim 1 where the first reference surface and the second reference surface are disposed in a recessed area of the first block.

3. The fixture of claim 1 where the first attaching mount comprises a first test specimen mounting recess in the first test specimen mounting portion and the second attaching mount comprises a second test specimen mounting recess in the second test specimen mounting portion and the third attaching mount comprises a third test specimen mounting recess in the third test specimen mounting portion and the fourth attaching mount comprises a fourth test specimen mounting recess in the third test specimen mounting portion.

4. The fixture of claim 1 where the first attaching mount comprises a first half-dog-bone-shaped mounting recess in the first test specimen mounting portion and the second attaching mount comprises a second half-dog-bone-shaped mounting recess in the second test specimen mounting portion and the third attaching mount comprises a third half-dog-bone-shaped mounting recess in third test specimen mounting portion and the fourth attaching mount comprises a fourth half-dog-bone-shaped mounting recess in the third test specimen mounting portion.

5. The fixture of claim 1 wherein the first angle is an acute angle.

6. The fixture of claim 1 wherein the first angle is 90° and the second angle is 90°.

7. A method of imposing near fracture stresses in a material test specimen comprising:
  (a) loading two substantially identical test specimens in a test fixture configured to impose substantially identical shear stresses in each test specimen;
  (b) applying a load force to the test fixture to impose the substantially identical shear stresses in the two test specimens until only one of the test specimens fractures; and
  (c) removing the load force prior to fracture of the test specimen not fractured in step (b).

8. The method of claim 7 wherein step (a) comprises loading two substantially identical test specimens in a test fixture configured to impose substantially identical shear and tensile stresses in each test specimen.

9. The method of claim 7 wherein step (a) comprises loading two substantially identical test specimens in a test fixture configured to impose substantially identical shear stresses at a structural transition zone in each test specimen.

10. The method of claim 7 wherein step (a) comprises loading two substantially identical test specimens in a test fixture configured to impose substantially identical shear and tensile stresses at a structural transition zone in each test specimen.

* * * * *